(12) United States Patent
Grode

(10) Patent No.: US 9,084,749 B2
(45) Date of Patent: Jul. 21, 2015

(54) RECOMBINANT MYCOBACTERIUM AS VACCINE FOR USE IN HUMANS

(75) Inventor: Leander Grode, Braunschweig (DE)

(73) Assignee: Vakzine Projekt Management GmbH, Hannover (DE)

( * ) Notice: Subject to any disclaimer, the term of this patent is extended or adjusted under 35 U.S.C. 154(b) by 0 days.

(21) Appl. No.: 13/822,706

(22) PCT Filed: Sep. 16, 2011

(86) PCT No.: PCT/EP2011/066131
§ 371 (c)(1),
(2), (4) Date: Mar. 13, 2013

(87) PCT Pub. No.: WO2012/038348
PCT Pub. Date: Mar. 29, 2012

(65) Prior Publication Data
US 2013/0280287 A1    Oct. 24, 2013

Related U.S. Application Data

(60) Provisional application No. 61/384,375, filed on Sep. 20, 2010.

(51) Int. Cl.
*A61K 39/04* (2006.01)
*A61K 39/00* (2006.01)

(52) U.S. Cl.
CPC ........... *A61K 39/04* (2013.01); *A61K 2039/523* (2013.01)

(58) Field of Classification Search
None
See application file for complete search history.

(56) References Cited

FOREIGN PATENT DOCUMENTS

| WO | 99/10496 A1 | 3/1999 |
|---|---|---|
| WO | WO2004/094469 A1 * | 11/2004 |
| WO | 2006/045468 A1 | 5/2006 |

OTHER PUBLICATIONS

Brosch et al. PNAS. Mar. 27, 2007. 104 (13): 5596-601.*
Brosch et al., "Genome plasticity of BCG and impact on vaccine efficacy", PNAS, Mar. 27, 2007, vol. 104, No. 13, pp. 5596-5601.
International Preliminary Report on Patentability, PCT/EP2011/066131, dated Mar. 26, 2013, 5 pages.
Eisele et al.: "Induction of antigen specific multifunctional T cells after vaccination with the live recombinant tuberculosis vaccine VPM1002 in a Phase I clinical trial", Jun. 2, 2010, XP002665473, Retrieved from the Internet: URL:http://www.egms.de/static/en/meetings/ kit2010/10kit018.shtml [retrieved on Dec. 9, 2011] the whole document.
Grode L et al: "Increased vaccine efficacy against tuberculosis of recombinant *Mycobacterium bovis* bacille Calmette-Guerin mutants that secrete listeriolysin", Journal of Clinical Investigation, American Society for Clinical Investigation, US, vol. 115, No. 9, Sep. 1, 2005, pp. 2472-2479, XP002360644,ISSN: 0021-9738, DOI: 10.1172/JCI24617 the whole document.
Hannes Schlender: "Novel tuberculosis vaccine in Germany in clinical phase", Sep. 11, 2008, XP002665474,Retrieved from the Internet: URL:http://www.eurekalert.org/pub_releases/2008-09/haog-ntv091108.php [retrieved on Dec. 9, 2011] the whole document.
Kaufmann S H E: "Novel tuberculosis vaccination strategies based on understanding the immune response", Journal of Internal Medicine, vol. 267, No. 4, Apr. 2010, pp. 337-353, XP002665475, ISSN: 0954-6820 p. 346, right-hand column—p. 347, left-hand column.
Kaufmann Stefan H E: "Learning from natural infection for rational tuberculosis vaccine design From basic science to translational research", Human Vaccines, vol. 6, No. 8, Aug. 2010, pp. 614-618, XP002665477, p. 617, left-hand column—middle column.
Okada Masaji et al: "Tuberculosis vaccine development the development of novel (preclinical) DNA vaccine", Human Vaccines, vol. 6, No. 4, Apr. 2010, pp. 297-308, XP002665476, the whole document.
Parida et al."Novel tuberculosis vaccines on the horizon", Current Opinion in Immunology, 2010, 22, pp. 374-384.
Hess et al., "*Mycobacterium bovis* bacille Calmette-Guerin strains secreting listeriolysin of *Listeria monocytogenes*", Proc. Natl. Acad. Sci., vol. 95, Apr. 1998, pp. 5299-5304.

* cited by examiner

*Primary Examiner* — Jennifer Graser
(74) *Attorney, Agent, or Firm* — Rothwell, Figg, Ernst & Manbeck, P.C.

(57) ABSTRACT

The invention relates to a recombinant vaccine providing protective immunity especially against tuberculosis in human subjects.

11 Claims, 5 Drawing Sheets

Figure 1:
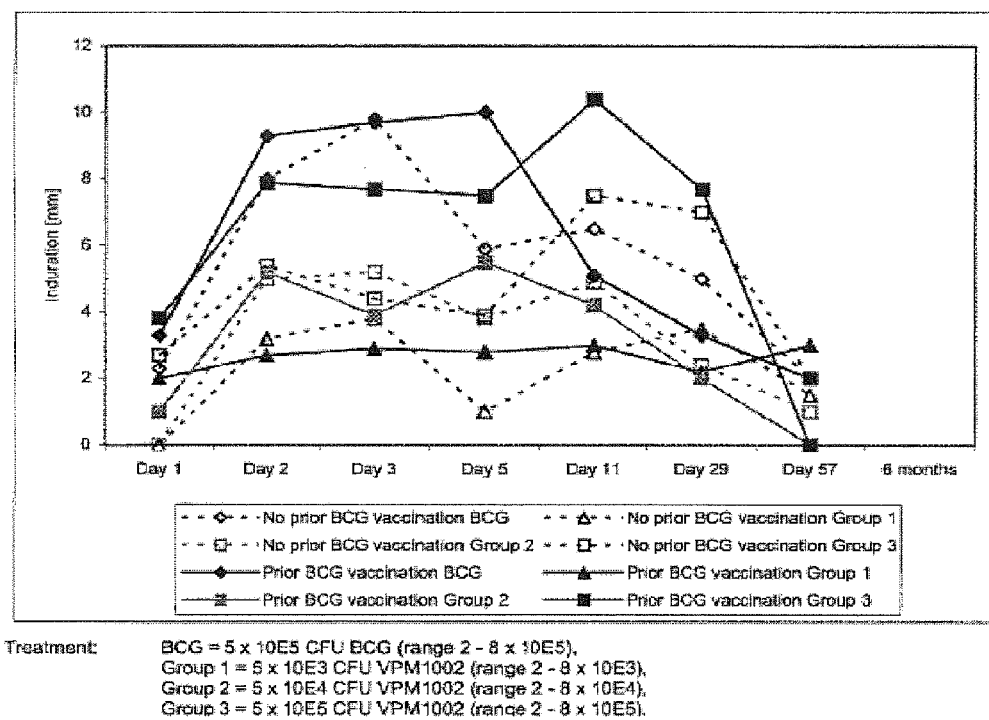

Mean Changes from Baseline for IFN-γ-Response after Stimulation with Ag85B in Naïve Subjects

Mean Changes from Baseline for IFN-γ-Response after Stimulation with Ag85B in Pre-Immunized Subjects

SEQUENCE LISTING

```
<160> NUMBER OF SEQ ID NOS: 2

<210> SEQ ID NO 1
<211> LENGTH: 1881
<212> TYPE: DNA
<213> ORGANISM: Artificial Sequence
<220> FEATURE:
<223> OTHER INFORMATION: recombinant nucleic acid molecule

<400> SEQUENCE: 1
atgacagacg tgagccgaaa gattcgagct tggggacgcc gattgatgat cggcacggca        60
gcggctgtag tccttccggg cctggtgggg cttgccggcg gagcggcaac cgcgggcgcg       120
ttctcccggc cggggctgcc ggtcgagtac ctgcagtctg caaagcaatc cgctgcaaat       180
aaattgcact cagcaggaca aagcacgaaa gatgcatctg cattcaataa agaaaattca       240
atttcatcca tggcaccacc agcatctccg cctgcaagtc ctaagacgcc aatcgaaaag       300
aaacacgcgg atgaaatcga taagtatata caaggattgg attacaataa aaacaatgta       360
ttagtatacc acggagatgc agtgacaaat gtgccgccaa gaaaaggtta caagatgga       420 aatgaatata ttgttgtgga gaaaaagaag aaatccatca atcaaaataa tgcagacatt       480
caagttgtga atgcaatttc gagcctaacc tatccaggtg ctctcgtaaa agcgaattcg       540
gaattagtag aaaatcaacc agatgttctc cctgtaaaac gtgattcatt aacactcagc       600
attgatttgc caggtatgac taatcaagac aataaaatcg ttgtaaaaaa tgccactaaa       660
```

-continued

```
tcaaacgtta caacgcagt aaatacatta gtggaaagat ggaatgaaaa atatgctcaa       720
gcttatccaa atgtaagtgc aaaaattgat tatgatgacg aaatggctta cagtgaatca       780
caattaattg cgaaatttgg tacagcattt aaagctgtaa ataatagctt gaatgtaaac       840
ttcggcgcaa tcagtgaagg gaaaatgcaa gaagaagtca ttagttttaa acaaatttac       900
tataacgtga atgttaatga acctacaaga ccttccagat ttttcggcaa agctgttact       960
aaagagcagt tgcaagcgct tggagtgaat gcagaaaatc ctcctgcata tatctcaagt      1020
gtggcgtatg gccgtcaagt ttatttgaaa ttatcaacta attcccatag tactaaagta      1080
aaagctgctt ttgatgctgc cgtaagcgga aaatctgtct caggtgatgt agaactaaca      1140
aatatcatca aaaattcttc cttcaaagcc gtaatttacg gaggttccgc aaaagatgaa      1200
gttcaaatca tcgacggcaa cctcggagac ttacgcgata ttttgaaaaa aggcgctact      1260
tttaatcgag aaacaccagg agttcccatt gcttatacaa caaacttcct aaaagacaat      1320
gaattagctg ttattaaaaa caactcagaa tatattgaaa caacttcaaa agcttataca      1380
gatggaaaaa ttaacatcga tcactctgga ggatacgttg ctcaattcaa catttcttgg      1440
gatgaagtaa attatgatcc tgaaggtaac gaaattgttc aacataaaaa ctggagcgaa      1500
aacaataaaa gcaagctagc tcatttcaca tcgtccatct atttgccagg taacgcgaga      1560
aatattaatg tttacgctaa agaatgcact ggtttagctt gggaatggtg agaacggta       1620
attgatgacc ggaacttacc acttgtgaaa atagaaata tctccatctg gggcaccacg       1680
ctttatccga aatatagtaa taaagtagat aatccaatcg aatatgcatt agcctatgga      1740
agtcagggtg atcttaatcc attaattaat gaaatcagca aaatcatttc agctgcagtt      1800
ctttcctctt taacatcgaa gctacctgca gagttcgtta ggcgcggatc cggaattcga      1860
agcttatcga tgtcgacgta g                                                 1881
```

<210> SEQ ID NO 2
<211> LENGTH: 626
<212> TYPE: PRT
<213> ORGANISM: Artificial Sequence
<220> FEATURE:
<223> OTHER INFORMATION: immunogenic polypeptide
<400> SEQUENCE: 2

```
Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Ser Ala Lys Gln Ser Ala Ala Asn Lys Leu His Ser
    50                  55                  60

Ala Gly Gln Ser Thr Lys Asp Ala Ser Ala Phe Asn Lys Glu Asn Ser
65                  70                  75                  80

Ile Ser Ser Met Ala Pro Pro Ala Ser Pro Ala Ser Pro Lys Thr
                85                  90                  95

Pro Ile Glu Lys Lys His Ala Asp Glu Ile Asp Lys Tyr Ile Gln Gly
            100                 105                 110

Leu Asp Tyr Asn Lys Asn Asn Val Leu Val Tyr His Gly Asp Ala Val
        115                 120                 125

Thr Asn Val Pro Pro Arg Lys Gly Tyr Lys Asp Gly Asn Glu Tyr Ile
    130                 135                 140
```

| | | | | | | | | | | | | |
|---|---|---|---|---|---|---|---|---|---|---|---|---|
|Val|Val|Glu|Lys|Lys|Lys|Ser|Ile|Asn|Gln|Asn|Asn|Ala|Asp|Ile|
|145| | | | |150| | | |155| | | |160|

Gln Val Val Asn Ala Ile Ser Ser Leu Thr Tyr Pro Gly Ala Leu Val
                165                 170                 175

Lys Ala Asn Ser Glu Leu Val Glu Asn Gln Pro Asp Val Leu Pro Val
            180                 185                 190

Lys Arg Asp Ser Leu Thr Leu Ser Ile Asp Leu Pro Gly Met Thr Asn
        195                 200                 205

Gln Asp Asn Lys Ile Val Val Lys Asn Ala Thr Lys Ser Asn Val Asn
    210                 215                 220

Asn Ala Val Asn Thr Leu Val Glu Arg Trp Asn Glu Lys Tyr Ala Gln
225                 230                 235                 240

Ala Tyr Pro Asn Val Ser Ala Lys Ile Asp Tyr Asp Asp Glu Met Ala
                245                 250                 255

Tyr Ser Glu Ser Gln Leu Ile Ala Lys Phe Gly Thr Ala Phe Lys Ala
            260                 265                 270

Val Asn Asn Ser Leu Asn Val Asn Phe Gly Ala Ile Ser Glu Gly Lys
        275                 280                 285

Met Gln Glu Glu Val Ile Ser Phe Lys Gln Ile Tyr Tyr Asn Val Asn
    290                 295                 300

Val Asn Glu Pro Thr Arg Pro Ser Arg Phe Phe Gly Lys Ala Val Thr
305                 310                 315                 320

Lys Glu Gln Leu Gln Ala Leu Gly Val Asn Ala Glu Asn Pro Pro Ala
                325                 330                 335

Tyr Ile Ser Ser Val Ala Tyr Gly Arg Gln Val Tyr Leu Lys Leu Ser
            340                 345                 350

Thr Asn Ser His Ser Thr Lys Val Lys Ala Ala Phe Asp Ala Ala Val
        355                 360                 365

Ser Gly Lys Ser Val Ser Gly Asp Val Glu Leu Thr Asn Ile Ile Lys
    370                 375                 380

Asn Ser Ser Phe Lys Ala Val Ile Tyr Gly Gly Ser Ala Lys Asp Glu
385                 390                 395                 400

Val Gln Ile Ile Asp Gly Asn Leu Gly Asp Leu Arg Asp Ile Leu Lys
                405                 410                 415

Lys Gly Ala Thr Phe Asn Arg Glu Thr Pro Gly Val Pro Ile Ala Tyr
            420                 425                 430

Thr Thr Asn Phe Leu Lys Asp Asn Glu Leu Ala Val Ile Lys Asn Asn
        435                 440                 445

Ser Glu Tyr Ile Glu Thr Thr Ser Lys Ala Tyr Thr Asp Gly Lys Ile
    450                 455                 460

Asn Ile Asp His Ser Gly Gly Tyr Val Ala Gln Phe Asn Ile Ser Trp
465                 470                 475                 480

Asp Glu Val Asn Tyr Asp Pro Glu Gly Asn Glu Ile Val Gln His Lys
                485                 490                 495

Asn Trp Ser Glu Asn Asn Lys Ser Lys Leu Ala His Phe Thr Ser Ser
            500                 505                 510

Ile Tyr Leu Pro Gly Asn Ala Arg Asn Ile Asn Val Tyr Ala Lys Glu
        515                 520                 525

Cys Thr Gly Leu Ala Trp Glu Trp Trp Arg Thr Val Ile Asp Asp Arg
    530                 535                 540

Asn Leu Pro Leu Val Lys Asn Arg Asn Ile Ser Ile Trp Gly Thr Thr
545                 550                 555                 560

Leu Tyr Pro Lys Tyr Ser Asn Lys Val Asp Asn Pro Ile Glu Tyr Ala

|     |     |     |     | 565 |     |     |     |     | 570 |     |     |     |     | 575 |     |     |
| --- | --- | --- | --- | --- | --- | --- | --- | --- | --- | --- | --- | --- | --- | --- | --- | --- |
| Leu | Ala | Tyr | Gly | Ser | Gln | Gly | Asp | Leu | Asn | Pro | Leu | Ile | Asn | Glu | Ile |
|     |     |     | 580 |     |     |     |     |     | 585 |     |     |     |     | 590 |     |
| Ser | Lys | Ile | Ile | Ser | Ala | Ala | Val | Leu | Ser | Ser | Leu | Thr | Ser | Lys | Leu |
|     |     | 595 |     |     |     |     | 600 |     |     |     |     | 605 |     |     |     |
| Pro | Ala | Glu | Phe | Val | Arg | Arg | Gly | Ser | Gly | Ile | Arg | Ser | Leu | Ser | Met |
|     |     | 610 |     |     |     | 615 |     |     |     |     | 620 |     |     |     |     |
| Ser | Thr |
| 625 |     |

RECOMBINANT MYCOBACTERIUM AS VACCINE FOR USE IN HUMANS

CROSS REFERENCE TO RELATED APPLICATION

This application is a 35 U.S.C. 371 National Phase Entry Application from PCT/EP2011/066131, filed Sep. 16, 2011, which claims the benefit of U.S. 61/384,375 filed on Sep. 20, 2010, the disclosure of which is incorporated herein in its entirety by reference.

REFERENCE TO A SEQUENCE LISTING

The present application includes a Sequence Listing filed in electronic format. The Sequence Listing is entitled "2923-1201_ST25.txt" created on Mar. 12, 2013, and is 9,000 bytes in size. The information in the electronic format of the Sequence Listing is part of the present application and is incorporated herein by reference in its entirety.

The invention relates to a novel recombinant vaccine providing protective immunity especially against tuberculosis in human subjects.

In 1993 tuberculosis (TB) has been declared a global emergency by World Health Organization (WHO). Worldwide approximately 2 billion people[1,2] are infected with *Mycobacterium tuberculosis*, the causative microorganism of TB. All are at risk of developing clinical symptoms of the disease. In most individuals infection with *Mycobacterium tuberculosis* is initially contained by host defences, and the infection remains latent. However, latent TB infection has the potential to develop into active TB disease at any time, and individuals with active TB become sources of new infections. In 2007 the number of new cases of disease was reported in WHO report (2009) to be 9.3 million[1] and is increasing steadily. Approximately 1.8 million people die from the disease each year. Thus, TB continues to be a leading cause of death by infectious disease worldwide.

BCG (Bacillus Calmette-Guérin), an attenuated strain of *Mycobacterium bovis*, has been in use as a TB vaccine since 1921. To date approximately 4 billion doses have been administered.[3] However, vaccination with BCG is insufficiently effective to stop the spread of TB. BCG can protect against, or at least ameliorate, severe forms of systemic TB in children, particularly meningitis. BCG does not protect against the pulmonary and infectious form of the disease.[4] This, however, would be necessary for the interruption of the transmission of the disease.

There are only a few antibiotic treatments available. They are increasingly failing, as more and more patients get infected with multi-drug resistant TB strains.[1,5] To make the situation even worse, new highly pathogenic strains, like *Mycobacterium tuberculosis* Beijing/W, are spreading.[6]

An object of the present invention is the development of a safe, well tolerated and efficacious vaccine against TB, particularly for residents in endemic areas and persons at risk in non-endemic areas. This vaccine is to replace the currently used BCG vaccine. The new vaccine should be at least as potent as the current strain and should be safer than BCG.[5,7]

*Mycobacterium tuberculosis* and BCG are phagocytosed by host macrophages. Intraphagosomal location causes bacterial antigen trafficking through the major histocompatibility complex (MHC) II pathway. This results in preferential stimulation of CD4 T cells. However, it has been shown that MHC I restricted CD8 cytotoxic T cells are crucial in immunity to *Mycobacterium tuberculosis*.[8,9] In contrast to *Mycobacterium tuberculosis*, BCG only induces weak stimulation of CD8 cytotoxic T cells.[2,3,10] Therefore, a recombinant BCG strain expressing a phagolysosomal escape domain was generated in order to direct mycobacterial antigens to the MHC I pathway.[2,7] The strain secretes listeriolysin (Hly) of *L. monocytogenes*.[7,11] It enables the strain to escape from the phagosome of infected host cells by perforating the membrane of the phagosome. Inactivation of the urease C gene was necessary to assure an acidic phagosomal pH for optimal Hly activity. Perforation promotes antigen translocation into the cytoplasm and facilitates cross-priming through increased apoptosis.[7,9] This process mimics the immune induction of *Mycobacterium tuberculosis* very effectively. The mode of action is expected to result in an efficacious and well tolerated vaccine against TB.

The concept has been described in WO99/101496 and in WO 2004/094469, the contents of which are herein incorporated by reference.

In this study a recombinant urease-deficient BCG vaccine was applied in human subjects for the first time. The study evaluated safety, local and systemic tolerability as well as the immunogenicity of the vaccine. It followed a dose-escalating sequential design with comparison to commercially available BCG. Eighty (80) subjects in Germany were randomly allocated to 4 groups consisting of 20 subjects each stratified for their history of BCG-vaccination.

Intensive safety monitoring including laboratory parameters, physical safety evaluations and detailed ECG-analysis was done in addition to standard safety monitoring.

A subject-matter of the present invention is a vaccine for use in humans comprising as an active ingredient a recombinant *Mycobacterium* which is urease-deficient and which comprises a recombinant nucleic acid molecule encoding a fusion polypeptide comprising (a) a *Mycobacterium* antigen or an immunogenic fragment thereof, and (b) a phagolysomal escape domain.

A further subject-matter of the present invention is a method for vaccinating a human subject, comprising administering a pharmaceutically effective dose of a recombinant *Mycobacterium* which is urease-deficient and which comprises a recombinant nucleic acid molecule encoding a fusion polypeptide comprising (a) a *Mycobacterium* antigen or an immunogenic fragment thereof, and (b) a phagolysosomal escape domain.

In an especially preferred embodiment the ureC sequence is inactivated (ΔUrec), e.g. by constructing a suicide vector containing a ureC gene disrupted by a selection marker gene, transforming the target cell with the vector and screening for selection marker-positive cells having a urease negative phenotype[12].

The cell is preferably an *M. bovis* cell, an *M. tuberculosis* cell, particularly an attenuated *M. tuberculosis* cell or other Mycobacteria, e.g. *M. microti, M. smegmatis, M. canettii, M. marinum* or *M. fortuitum*. More preferably, the cell is a recombinant *M. bovis* (BCG) cell, particularly a recombinant *M. bovis* cell from strain Danish subtype Prague[13]. Most preferably, the cell is recombinant BCG strain Danish subtype Prague characterized as rBCG ΔUrec::Hly+::Hyg+ (VPM 1002).

The *Mycobacterium* cell of the invention comprises a recombinant nucleic acid molecule, e.g. the nucleic acid molecule in SEQ ID No.1. This nucleic acid molecule comprises a signal peptide coding sequence (nucleotide 1-120), a sequence coding for an immunogenic domain (nucleotide 121-153), a peptide linker coding sequence (nucleotide 154-210), a sequence coding for a phagolysosomal domain (nucleotide 211-1722), a further peptide linker coding sequence (nucleotide 1723-1800) and a sequence coding for a random peptide (nucleotide 1801-1870). The corresponding amino acid sequence is shown in SEQ ID No.2.

The domain capable of eliciting an immune response is selected from immunogenic peptides or polypeptides from *M. bovis* or *M. tuberculosis* or from immunogenic fragments thereof having a length of at least 6, preferably at least 8 amino acids. Specific examples for suitable antigens are Ag85B (p30) from *M. tuberculosis* (Harth et al., 1996), Ag85B (α-antigen) from *M. bovis* BCG (Matsuo et al., 1988), Ag85A from *M. tuberculosis* (Huygen et al., 1996) and ESAT-6 from *M. tuberculosis* (Sorensen et al., 1996, Harboe et al., 1996 and Andersen et al., 1995). More preferably, the immunogenic domain is derived from the antigen Ag85B. Most preferably, the immunogenic domain comprises the sequence from aa.41 to aa.51 in SEQ ID No.2.

The recombinant nucleic acid molecule further comprises a phagolysosomal escape domain, i.e. a polypeptide domain which provides for an escape of the fusion polypeptide from the phagolysosome into the cytosol of mammalian cells. Preferably, the phagolysosomal escape domain is a *Listeria* phagolysosomal escape domain, which is described in U.S. Pat. No. 5,733,151, herein incorporated by reference. More preferably, the phagolysosomal escape domain is derived from the listeriolysin gene (Hly) of *L. monocytogenes*. Most preferably, the phagolysosomal domain is encoded by a nucleic acid molecule selected from: (a) a nucleotide sequence comprising nucleotides 211-1722 as shown in SEQ ID No.1, (b) a nucleotide sequence which encodes for the same amino acid sequence as the sequence from (a), and (c) a nucleotide sequence hybridizing under stringent conditions with the sequence from (a) or (b).

Apart from the nucleotide sequence depicted in SEQ ID No.1 the present invention also comprises nucleic acid sequences hybridizing therewith. In the present invention the term "hybridization" is used as defined in Sambrook et al. (Molecular Cloning. A laboratory manual, Cold Spring Harbor Laboratory Press (1989), 1.101-1.104). In accordance with the present invention the term "hybridization" is used if a positive hybridization signal can still be observed after washing for one hour with 1×SSC and 0.1% SDS at 55° C., preferably at 62° C. and more preferably at 68° C., particularly for 1 hour in 0.2×SSC and 0.1% SDS at 55° C., preferably at 62° C. and more preferably at 68° C. A sequence hybridizing with a nucleotide sequence as per SEQ ID No.1 under such washing conditions is a phagolysosomal escape domain encoding nucleotide sequence preferred by the subject invention.

A nucleotide sequence encoding a phagolysosomal escape domain as described above may be directly obtained from a *Listeria* organism or from any recombinant source e.g. a recombinant *E. coli* cell containing the corresponding *Listeria* nucleic acid molecule or a variant thereof as described above.

Preferably, the recombinant nucleic acid molecule encoding for a fusion polypeptide contains a signal peptide encoding sequence. More preferably, the signal sequence is a signal sequence active in Mycobacteria, preferably in *M. bovis*, e.g. a native *M. bovis* signal sequence. A preferred example of a suitable signal sequence is the nucleotide sequence coding for the Ag85B signal peptide which is depicted in SEQ ID No.1 from nucleotide 1 to 120.

Further, it is preferred that a peptide linker be provided between the immunogenic domain and the phagolysosomal escape domain. Preferably, said peptide linker has a length of from 5 to 50 amino acids. More preferably, a sequence encoding a linker as shown in SEQ ID No.1 from nucleotide 154 to 210 or a sequence corresponding thereto as regards the degeneration of the genetic code.

The nucleic acid may be located on a recombinant vector. Preferably, the recombinant vector is a prokaryotic vector, i.e. a vector containing elements for replication or/and genomic integration in prokaryotic cells. Preferably, the recombinant vector carries the nucleic acid molecule of the present invention operatively linked with an expression control sequence. The expression control sequence is preferably an expression control sequence active in Mycobacteria, particularly in *M. bovis*. The vector can be an extrachromosomal vector or a vector suitable for integration into the chromosome. Examples of such vectors are known to the man skilled in the art and, for instance, given in Sambrook et al. supra.

In some embodiments, the recombinant *Mycobacterium* cell may carry an antibiotic resistance gene, e.g. a hygromycin (Hyg) resistance gene. In other embodiments, the recombinant *Mycobacterium* cell does not carry an antibiotic resistance gene.

Preferably, the vaccine is a live-vaccine for use in humans, e.g. for use in residents in areas endemic for mycobacterial infections, such as tuberculosis or for use in persons at risk in non-endemic areas. The vaccine may be for administration to a *Mycobacterium*, e.g. BCG-naïve subject, e.g. a human who has not been pre-exposed to an immunogenic *Mycobacterium* challenge or a human who has not been pre-immunized with BCG. Examples of such subjects are e.g. newborns or children, e.g. up to 8 years, e.g. in areas endemic for mycobacterial infections, such as tuberculosis, or persons at risk in non-endemic areas. The vaccine is particularly suitable for administration to subjects with HIV-positive parents, e.g. mothers. The vaccine may be administered to *Mycobacterium*-, e.g. BCG-, naïve subjects in a population endemic for HIV-infections. In other embodiments, the vaccine may be for administration to a *Mycobacterium*, e.g. BCG, pre-exposed subject, e.g. children from 9 years on or adults, e.g. living in areas with endemic tuberculosis or subjects pre-immunized with BCG. In such subjects the inventive vaccine has a boosting effect on already existing BCG induced immune status.

In a further preferred embodiment administration of the vaccine results in an increased IFN-γ response in naïve or pre-immunized subjects and in an upregulation of CD4$^+$ T cells, particularly of multifunctional CD4$^+$ T cells.

In a preferred embodiment, the vaccine is a lyophilisate comprising the *Mycobacterium* cell and optionally agents, e.g. glucose and/or dextran. Optionally the vaccine additionally comprises a reconstitution fluid, water for injection or saline. In some embodiments, the vaccine comprises a dose of about $10^3$-$10^4$ CFU (colony forming units), about $10^4$-$10^5$ CFU or about $10^5$-$10^6$ CFU.

Administration to a mucosal surface (e.g. ocular, intranasal, oral, gastric, intestinal, rectal, vaginal or urinary tract) or via the parenteral route (e.g. subcutaneous, intradermal, intramuscular, intravenous or intraperitoneal) might be chosen. Especially preferred is intradermal administration.

In some embodiments, the vaccine is for administration in a single dose including an immunization of Mycobacterium-naïve subjects or a booster vaccination of Mycobacterium-pre-exposed subjects, e.g. subjects who have been pre-vaccinated with a Mycobacterium-based vaccine, e.g. a native BCG vaccine for subjects who have come into contact with Mycobacteria, e.g. pathogenic Mycobacteria before administration of the inventive vaccine. Alternatively, the vaccine of the invention may be administered in two or more doses. The respective doses may be administered between intervals of about 1 week to about 6 months or longer.

The vaccine of the present invention is for use against Mycobacterial infections, more particularly for use against tuberculosis.

The invention will be further illustrated by the following Figures, Sequence Listings and Examples.

FIG. 1: Mean Induration Size by Treatment Group and Study Day

Figure 2:
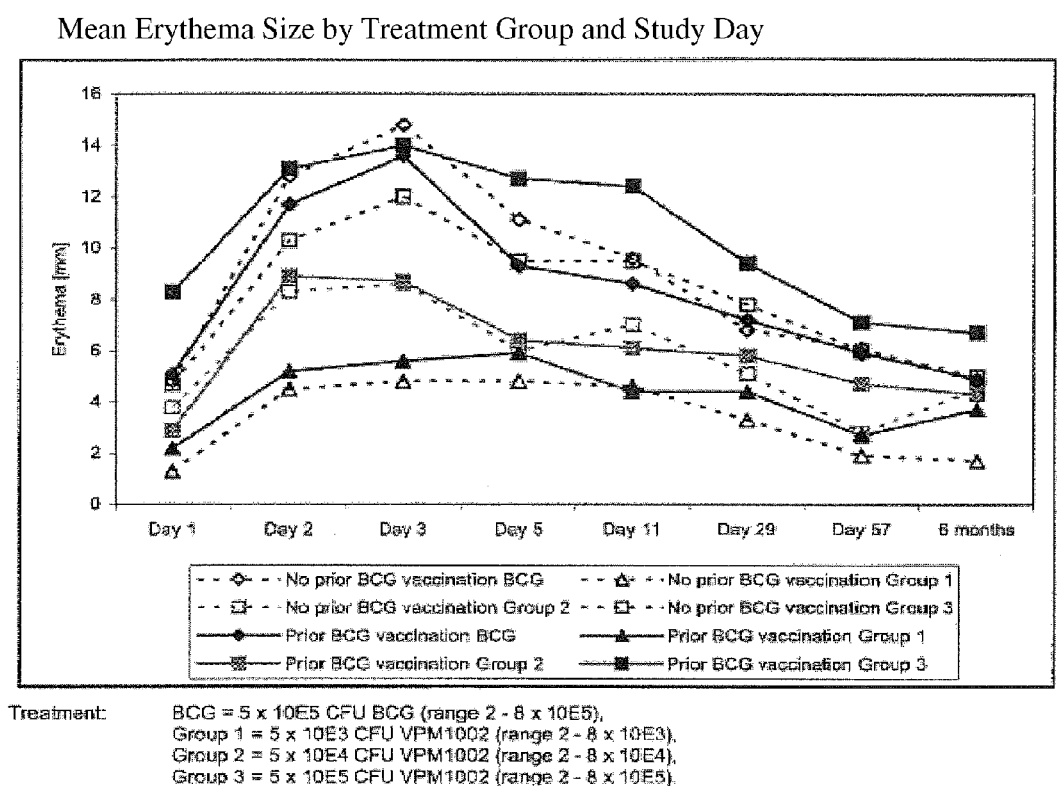

FIG. 2: Correlation of Mean Erythema Size by Treatment Group and Study Day

Figure 3:
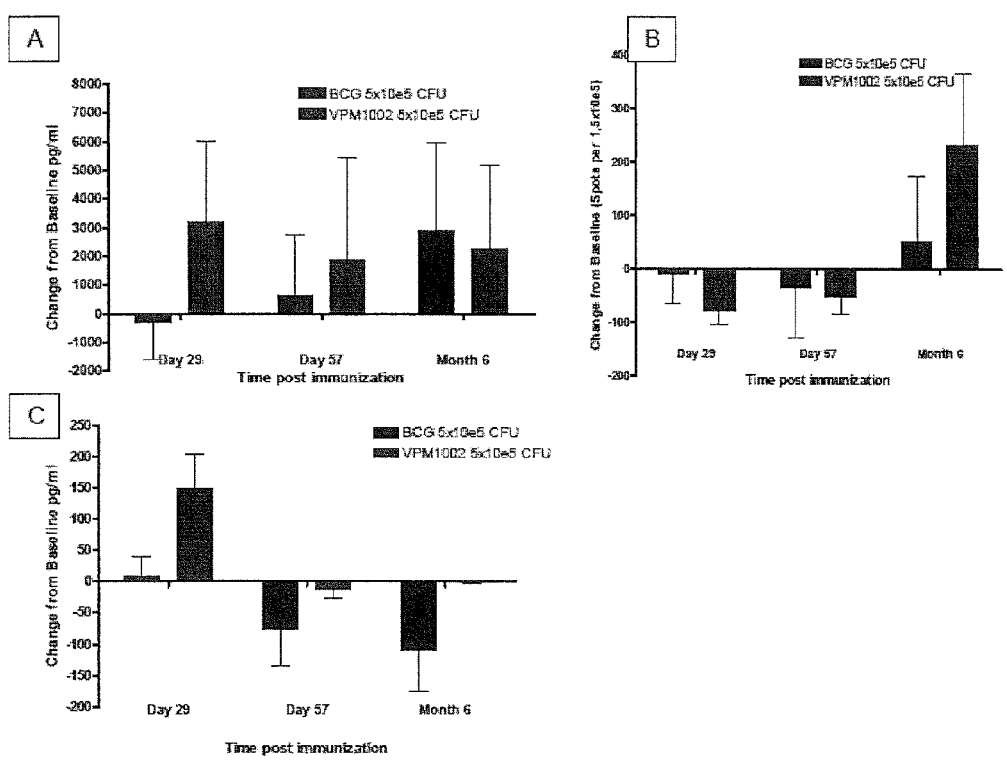

FIG. 3: Mean Changes from Baseline for IFN-γ-Response after Stimulation with Ag 85B in Naïve Subjects.
A. PBMC ELISA for IFN-γ,
B. ELISpot,
C. Whole blood ELISA for IFN-γ.
All assays have been stimulated with Ag85B 2 µg/mL. The VPM1002 ($5 \times 10^5$) in red bars, BCG group in blue bars. Stimulation: Ag 85B 2 µg/mL. VPM1002 increases the IFN-γ response.

Figure 4:
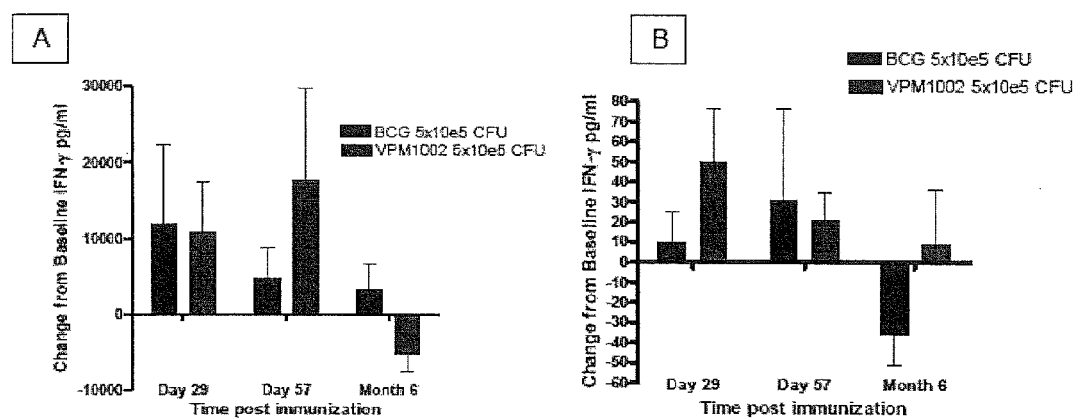

FIG. 4: Mean Changes from Baseline for IFN-γ Response after Stimulation with Ag 85B in Pre-Immunized Subjects
A. PBMC ELISA for IFN-γ,
B. Whole blood ELISA for IFN-γ.
All assays have been stimulated with Ag85B 2 µg/mL. The VPM1002 ($5 \times 10^5$) in red bars, BCG group in blue bars. Stimulation: Ag 85B 2 µg/mL. VPM1002 increases the IFN-γ response.

Figure 5:
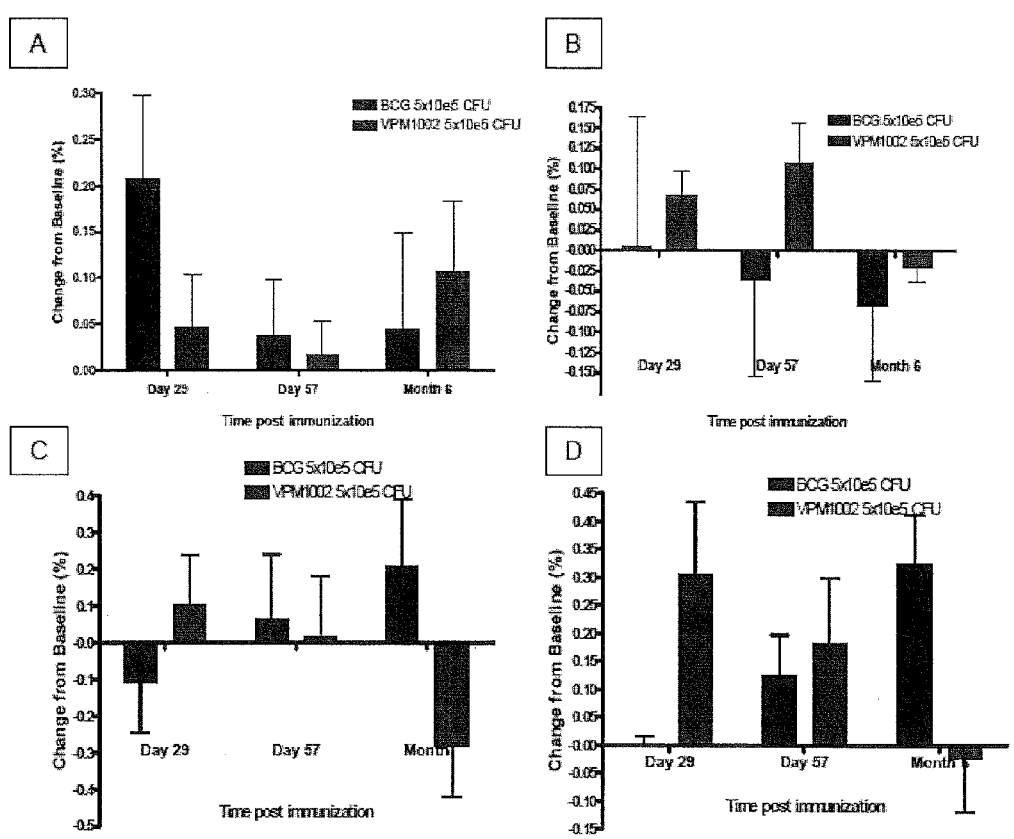

FIG. 5: Change from Baseline of Single and Multifunctional CD4$^+$ T cells in Naïve Subjects
A. The frequency of single positive CD4+ T cells (expression of IFN-γ) re-stimulated with PPD
B. Frequency of multifunctional CD4 T cells (expression of IFN-γ and IL-2) re-stimulated with Ag85B.
C. Frequency of multifunctional CD4 T cells (expressing IFN-γ, IL-2 and TNF-α) re-stimulated with PPD or
D. Re-stimulated with Ag85B, was determined by FACS ICS of PBMC from adults immunized with VPM1002 (red) or BCG control (blue).

SEQ ID No.1: shows the nucleotide sequence of a nucleic acid molecule encoding a Mycobaterium 85B antigen and a listeria phage-lysomal escape domain.

SEQ ID No.2: shows the corresponding amino acid sequence of the nucleic acid molecule of SEQ ID No.1.

EXAMPLE

Clinical Phase 1 Study to evaluate safety and immunogenicity of an inventive vaccine (VPM1002) in comparison with BCG in healthy male volunteers stratified for history of BCG vaccination.

1. Identity of the Vaccine VPM 1002

VPM1002 is a genetically modified BCG vaccine derived from the Mycobacterium bovis BCG strain Danish subtype Prague characterised as rBCG ΔureC::Hyg$^+$. VPM1002 was available as a lyophilised cake of live Mycobacterium bovis BCGΔureC::Hly$^+$::Hyg$^+$. One vial contained $5 \times 10^6$ CFU (range $2-8 \times 10^6$ CFU) of VPM1002.

The gene for listeriolysin (Hly) has been incorporated into the urease C gene (ureC) which results in deletion of the urease C activity and introduction of listeriolysin activity.

VPM1002 is resistant to hygromycin (Hyg). Hygromycin resistance served as a selection marker during genetic engineering of the strain and will serve as specific marker in the genetically modified organism (GMO)-monitoring and GMO-emergency-plan. VPM1002 is sensitive to antibiotics commonly used in treatment of mycobacterial infection, i.e. isoniazid, rifampicin and ethambutol.

VPM1002 was supplied as a freeze dried (lyophilized) cake which was reconstituted with 1 mL H$_2$O (aqua ad injectabilia). The concentration after reconstitution was about $5 \times 10^6$ CFU. For administration of doses of $5 \times 10^3$ and $5 \times 10^4$ CFU, the reconstituted VPM1002 suspension was diluted 1:100 or 1:10, respectively, using sterile ready to use sodium chloride 0.9% solution.

2. Objectives

The primary objective of this study was to investigate the safety of single doses of VPM1002.

The secondary objective of this study was to investigate the immunogenicity of single doses of VPM1002 for vaccination against Tuberculosis.

3. Methodology (Design of Study):

This was the first application of VPM1002 to humans. The study followed an open, randomised, controlled, dose-escalation design to assess the safety and immunogenicity of a single dose of VPM1002.

A single vaccination with VPM1002 was administered intra-dermally to subjects who were either Bacille Calmette-Guérin (BCG) naïve or had a pre-immunization with BCG (documented BCG-vaccination in the vaccination documents or BCG-scar and in both cases plus purified protein derivative (PPD)-skin-test not more than weakly positive). Three escalating doses of VPM1002 were investigated. A reference group of subjects received a single dose of BCG vaccine.

Following vaccination safety parameters were closely monitored until 4 hours after dosing. Thereafter the subjects were discharged from the clinic, except for the first 3 subjects within each dose group, who stayed in the clinic until 24 hours after vaccination.

Safety and pharmacodynamic assessments were performed until Day 57 and again 6 months after vaccination.

An interim safety analysis was performed after the results of Day 57 were available from the first 3 subjects of each cohort. Based on these data the administration of VPM1002 in doses up to $5 \times 10^5$ CFU was regarded as safe and well tolerated. Based on the secondary study endpoints of immunogenicity a statistic re-estimation of the sample size was performed. The results of this analysis (p1=0.0119) showed that the planned sample size of 80 subjects included in the study was sufficient. An extension of the sample size was not necessary.

4. Number of Subjects

Forty (40) BCG naïve and 40 subjects with BCG previous vaccination (or PPD positive) were planned to be included in this study. All 80 subjects, except for 1 subject, who was lost to follow-up, completed the study as planned.

| | Study cohorts | | | | | | | | |
|---|---|---|---|---|---|---|---|---|---|
| | no prior BCG-vaccination and PPD-negative | | | | prior BCG-vaccination or PPD-positive | | | | |
| | Treatment group | | | | | | | | |
| | BCG n (%) | Group 1 n (%) | Group 2 n (%) | Group 3 n (%) | BCG n (%) | Group 1 n (%) | Group 2 n (%) | Group 3 n (%) | Overall n (%) |
| Subjects included | 10 | 10 | 10 | 10 | 10 | 10 | 10 | 10 | 80 |
| Subjects completed | 10 (100) | 10 (100) | 10 (100) | 10 (100) | 10 (100) | 10 (100) | 10 (100) | 9 (90) | 79 (98.8) |
| Subjects withdrawn | 0 | 0 | 0 | 0 | 0 | 0 | 0 | 1 (10) | 1 (1.3) |
| Reason Other reasons | — | — | — | — | — | — | — | 1 (10) | 1 (1.3) |

Treatment: BCG = $5 \times 10E5$ CFU BCG (range $2\text{-}8 \times 10E5$), Group 1 = $5 \times 10E3$ CFU VPM1002 (range $2\text{-}8 \times 10E3$) Group 2 = $5 \times 10E4$ CFU VPM1002 (range $2\text{-}8 \times 10E4$), Group 3 = $5 \times 10E5$ CFU VPM1002 (range $2\text{-}8 \times 10E5$)

5. Diagnosis and Main Criteria for Inclusion:

Healthy male subjects, aged 18-55 years (extremes included), without any symptoms, physical signs or laboratory values suggestive of systemic disorders or current illness and without any signs of active or latent tuberculosis infection (LTBI). The tuberculin-PPD test had to be <10 mm for subjects with previous BCG vaccination and <1 mm for naïve subjects at baseline.

6. Test Product, Dose and Mode of Administration, Batch Number:

The active ingredient of VPM1002 was *Mycobacterium bovis* rBCGΔ ureC::Hly$^+$::Hyg$^+$, freeze-dried and standardised to number of viable (colony forming units (CFU)) mycobacteria per application.

Dose levels:
$5 \times 10^3$ CFU VPM1002 (range $2\text{-}8 \times 10^3$ CFU)
$5 \times 10^4$ CFU VPM1002 (range $2\text{-}8 \times 10^4$ CFU)
$5 \times 10^5$ CFU VPM1002 (range $2\text{-}8 \times 10^5$ CFU)

Approximately 0.1 mL reconstituted and diluted VPM1002 suspension was administered via intra-dermal injection with a syringe of 1 mL subgraduated into hundredths of mL (1/100 mL) fitted with a short bevel needle (25 G/0.50 mm or 26 G/0.45 mm, 10 mm in length). No jet injectors or multiple puncture device was allowed.

7. Duration of Treatment:
One single vaccination

8. Reference Therapy, Dose and Mode of Administration, Batch Number:

BCG Vaccine SSI, powder and solvent for suspension for injection, Statens Serum Institut Denmark.

After reconstitution, 1 dose (0.1 mL) contained:
*Mycobacterium bovis* BCG (Bacillus Calmette-Guérin), Danish strain 1331, live attenuated, $2\text{-}8 \times 10^5$ CFU.

Administration was performed as described for VPM1002.

9. Criteria of Evaluation:
Safety Parameters:
 incidence of adverse events, time profile of adverse events, other profile of adverse events
 assessment of local reaction at the vaccination site and photodocumentation of local reaction at the vaccination site (Days 1, 5, 11, 29, 57, after 6 months)
 standard safety laboratory parameters (haematology, coagulation, clinical chemistry including liver enzymes, urinalysis)
 QuantiFeron gold test at baseline, Day 57 and Month 6
 physical examination including electrocardiogram (ECG), vital signs and body weight
 chest-X-ray
 sonographic liver imaging at baseline, Day 57 and Month 6
 subjects' global assessment of tolerability.

Immunogenicity Parameters:
 lymphocyte stimulation test (LST): amount of interferon (IFN)-γ per cell
 enzyme linked immuno spot technique (ELIspot): number of IFN-γ secreting peripheral blood mononuclear cells (PBMC) per total number of PBMC
 whole blood assays (WBA): amount of IFN-γ per number of lymphocytes
 intracellular cytokine staining (ICS) (fluorescence activated cell sorting (FACS)-analysis): number of CD4+ and CD8+ lymphocytes; that were xxx-bright, xxx-bright and xxxbright ("triple-positive-cells"); per total number of lymphocytes.

10. Study Endpoints:
Primary Endpoint:

To assess the safety of a single dose of VPM1002 as assessed by physical examination, vital signs, ECG, liver sonography, chest X-ray, laboratory safety parameters (including haematology, coagulation, clinical chemistry and urinalysis), tolerability, recording of concomitant medication and monitoring of adverse events.

Secondary Endpoints:
 Immunogenicity, assessed by
  LST for tuberculin (PPD) with subsequent IFN-γ specific enzyme linked immunosorbent assay (ELISA) on supernatants of PBMC.
  ELIspot specific for the number of IFN-γ secreting PBMC after stimulation with PPD.
  WBA stimulating cells for 3 days with PPD and measuring IFN-γ in the plasma by ELISA.

Exploratory Endpoints:
 Immunogenicity, assessed by
  FACS-analysis of ICS for IFN-γ, tumour necrosis factor (TNF)-α and interleukin (IL)-2 in CD4+ and CD8+ lymphocytes upon overnight stimulation with PPD.
  FACS-analysis of intracellular staining with carboxyfluorescein diacetate succinimidyl esters (CFSE) in CD4+ and CD8+ lymphocytes upon overnight stimulation with PPD
  LST, ELIspot, ICS and WBA for stimulation with the tuberculosis antigen (TB-Ag) 85b peptide cocktail.
  Concentration of serum antibodies against PPD or the TB-Ag85B peptide cocktail; quantification of the immunoglobulin (Ig)G-subtypes of these serum antibodies.

11. Statistical Methods:

Descriptive statistics was used for evaluation of safety parameters. Following statistical test procedures were used for immunogenicity data:

Jonckheere Terpstra test ($\alpha=0.05$) for detecting a dose-response relationship in the adjusted changes from baseline in a repeated measurement setting in comparison with the BCG-group Linear regression model for adjusting changes from baseline to individual visits after baseline in the respective parameter with prospectively defined putative covariates and cofactors of the treatment factor (Backward selection)

Estimate of treatment effects (changes from baseline) using 95% confidence intervals, both within groups and comparing VPM1002-groups with the BCG-group Backward elimination of statistically irrelevant covariates/cofactors in the adjusting regression models X 2-test, t-test, U-test for exploratory comparisons between two treatment groups multivariate linear regression instead of Jonckheere-Terpstra-test estimating the sensitivity of the non-parametrical analyses 12. Summary Study Population:

All 80 subjects were included in the safety population and the Intention to Treat (ITT) population. All 80 subjects provided valid and interpretable assessments for immunogenicity parameters and had no major protocol deviation; therefore all subjects were valid for the Immunogenicity (IM) and the Per-Protocol (PP) population.

Overall mean age was 33.1 years (means for the different cohorts between 25.2 and 38.7 years). Mean height was 179.7 cm (between 177.2 and 181.8 cm), mean weight was 78.8 kg (between 73.0 and 82.5 kg) and mean BMI was 24.38 kg/m$^2$ (between 22.98 and 25.78 kg/m$^2$). Differences between the treatment groups were considered not clinically relevant.

13. Summary Pharmcodynamics:

The secondary objective of this study was to show the immunogenicity of VPM1002. The secondary objective was met. The study shows that VPM1002 induces quantitatively and qualitatively very good cellular immune responses in both strata the "naïve" and the BCG "pre-immunized" subjects. All observed data show a clear Th1 type immune response elicited by VPM1002. The initial goal of the development of that particular vaccine strain VPM1002 was to increase the cell mediated immune response and to induce qualitatively better immune responses than BCG. These goals could be met. In addition it shows also a potential for a boost vaccination on a pre-existing immune response induced by BCG.

For the amount of IFN-$\gamma$ per number of lymphocytes (secondary endpoints LST and WBA) a dose-response correlation was observed between the groups who received VPM1002 by non-parametric and parametric statistics. Within each stratum, mean changes from baseline were highest in the $5 \times 10^5$ CFU VPM1002 group and lowest in the $5 \times 10^3$ CFU VPM1002 on all study days. This proves the effect of VPM1002 to the recipient.

The linear regression analysis of the changes from baseline in the secondary endpoints showed that age, weight, total PBMC at baseline and total lymphocytes at baseline had no statistical significant effect on the results.

In the exploratory endpoints a considerable effect on induction of multifunctional CD4+ T cells was observed in both strata.

To conclude, VPM1002 elicits a Th1 immune response by inducing IFN-$\gamma$, not only quantitatively different from BCG but also qualitatively different with multifunctional T cells. These results encourage the further development of the vaccine.

14. Summary Safety:

The primary endpoint of this phase I study was the safety-assessment of VPM1002. Indeed, the study did not reveal any safety concerns for VPM1002.

In detail, single vaccination with up to $5 \times 10^5$ CFU VPM1002 was well tolerated. No Serious Adverse Event (AE) occurred.

Overall 80.7% of all AEs were considered as related to the study medication (adverse drug reactions (ADRs): relationship assessed as "certain", "probable" or "possible") by the investigator.

ADRs were reported by all subjects. Almost all ADR were injection site disorders (98.0% of all ADRs).

The number of ADRs increased with increasing dose. However, the frequency and intensity of ADRs was always medically acceptable, even at the highest dose of VPM1002 ($5 \times 10^5$ CFU). There was also a tendency towards a higher incidence of ADRs in subjects with previous BCG vaccination as compared to the respective treatment groups without BCG pre-immunization (239 vs. 204 ADRs, respectively).

All subjects experienced AE. The number of AEs was similar in the BCG and the $5 \times 10^5$ CFU VPM1002 groups in subjects not pre-immunized with BCG vaccination (76 and 82 AEs, respectively) and lower in the 2 other groups (47 AEs after $5 \times 10^3$ CFU VPM 1002 and 53 AEs after $5 \times 10^4$ CFU VPM 1002). In the group of subjects with prior BCG vaccination the number of AEs was highest in the $5 \times 10^5$ CFU VPM1002 group (97 AEs), compared to 72 AEs in the BCG group and 61 AEs in both the $5 \times 10^3$ CFU and $5 \times 10^4$ CFU VPM1002 groups.

Within the stratum of BCG-naïve subjects ADRs observed in the treatment groups that received BCG and VPM1002 in the same dose range ($5 \times 10^5$ CFU) were of comparable incidence and severity (64 versus 72 after BCG and VPM1002, respectively). Within the stratum of BCG pre-immunized subjects the incidence of ADRs was slightly higher in subjects who received $5 \times 10^5$ CFU VPM1002 compared to $5 \times 10^5$ CFU BCG (78 ADRs after VPM1002 versus 60 ADRs after BCG). However the intensity of ADRs was comparable between both cohorts and upon closer inspection the main reason for this imbalance seems to be a slightly higher incidence of injection site ulceration after VPM1002 (4 and 8 events after BCG and VPM1002, respectively; 1 to 8 mm in diameter) associated with related follow-up events like scabbing, and exfoliation at the injection site (6 versus 9 and 4 versus 7 ADRs, respectively, after BCG and VPM1002), all rated to be mild in intensity and being another indicator of induction of immunogenicity.

Most AEs were of mild intensity (95.3% of all AE), 25 AEs (4.6% of all AE) were of moderate intensity and 1 AE (0.1% of all AE, reported after BCG) was of severe intensity.

No subject discontinued due to an AE.

| | Summary of Overall Number of AEs and Injection Site Disorders | | | | | | | |
|---|---|---|---|---|---|---|---|---|
| | no prior BCG-vaccination and PPD-negative | | | | prior BCG-vaccination or PPD-positive | | | |
| System Organ Class<br>Preferred Term | BCG<br>n = 10<br>x (y, z %) | Group 1<br>n = 10<br>x (y, z %) | Group 2<br>n = 10<br>x (y, z %) | Group 3<br>n = 10<br>x (y, z %) | BCG<br>n = 10<br>x (y, z %) | Group 1<br>n = 10<br>x (y, z %) | Group 2<br>n = 10<br>x (y, z %) | Group 3<br>n = 10<br>x (y, z %) |
| Overall | 76 (10, 100) | 47 (10, 100) | 53 (10, 100) | 82 (10, 100) | 72 (10, 100) | 61 (10, 100) | 61 (10, 100) | 97 (10, 100) |
| | General disorders and administration site conditions | | | | | | | |
| Total | 63 (10, 100) | 30 (10, 100) | 34 (10, 100) | 68 (10, 100) | 60 (10, 100) | 46 (10, 100) | 51 (10, 100) | 72 (10, 100) |
| Injection site discomfort | — | — | — | — | 1 (1, 10.0) | — | 1 (1, 10.0) | 2 (2, 20.0) |
| Injection site erythema | 11 (10, 100) | 10 (10, 100) | 10 (10, 100) | 10 (10, 100) | 10 (10, 100) | 10 (10, 100) | 10 (10, 100) | 10 (10, 100) |
| Injection site exfoliation | 3 (3, 30.0) | — | — | 7 (7, 70.0) | 4 (4, 40.0) | 2 (2, 20.0) | 4 (4, 40.0) | 7 (7, 70.0) |
| Injection site induration | 12 (10, 100) | 13 (8, 80.0) | 12 (10, 100) | 13 (10, 100) | 15 (10, 100) | 14 (10, 100) | 11 (10, 100) | 14 (10, 100) |
| Injection site pain | 3 (3, 30.0) | 1 (1, 10.0) | 2 (2, 20.0) | 4 (4, 40.0) | 2 (2, 20.0) | 2 (2, 20.0) | — | 4 (4, 40.0) |
| Injection site pruritus | 7 (7, 70.0) | 2 (2, 20.0) | 3 (3, 30.0) | 7 (7, 70.0) | 7 (7, 70.0) | 4 (3, 30.0) | 6 (5, 50.0) | 7 (7, 70.0) |
| Injection site scab | 9 (6, 60.0) | 1 (1, 10.0) | 2 (2, 20.0) | 9 (8, 80.0) | 6 (5, 50.0) | 5 (4, 40.0) | 8 (7, 70.0) | 9 (8, 80.0) |
| Injection site swelling | 11 (8, 80.0) | 2 (2, 20.0) | 4 (4, 40.0) | 13 (8, 80.0) | 10 (6, 60.0) | 5 (4, 40.0) | 8 (6, 60.0) | 11 (9, 90.0) |
| Injection site ulcer | 6 (5, 50.0) | 1 (1, 10.0) | 1 (1, 10.0) | 5 (5, 50.0) | 4 (4, 40.0) | 2 (2, 20.0) | 3 (3, 30.0) | 8 (8, 80.0) |
| Injection site abscess | — | — | — | — | 1 (1, 10.0) | — | 2 (2, 20.0) | 3 (3, 30.0) |
| Injection site pustuie | 1 (1, 10.0) | — | 1 (1, 10.0) | 3 (3, 30.0) | — | — | — | 3 (3, 30.0) |

Treatment: BCG = 5 × 10E5 CFU BCG (range 2-8 × 10E5), Group 1 = 5 × 10E3 CFU VPM1002 (range 2-8 × 10E3), Group 2 = 5 × 10E4 CFU VPM1002 (range 2-8 × 10E4), Group 3 = 5 × 10E5 CFU VPM1002 (range 2-8 × 10E5).

Overall, the number of subjects with local reactions and the intensity of local reaction increased with increasing dose and were comparable for the 5×10$^5$ CFU BCG and VPM1002 groups. Results in BCG naïve subjects and subjects pre-immunized with BCG were generally similar, no clear trend to a different local reaction was observed. The most prominent local reactions were erythema and induration. Erythema was observed in all subjects. The to mean size of the erythema increased with dose. The mean erythema size was similar after vaccination with 5×10$^5$ CFU BCG and VPM1002. In subjects who received 5×10$^5$ CFU VPM1002 mean erythema size was consistently higher in pre-immunized subjects, whereas in the BCG group mean size was higher in the subject group without prior BCG-immunization.

No clear dose-relationship was observed for the number of subjects with induration. The mean size of induration was highest in the treatment groups, who received 5×10$^5$ CFU BCG or VPM1002. The maximum induration occurred in the groups vaccinated with 5×10$^5$ CFU BCG around day 3 to 5 which was earlier than in the groups vaccinated with 5×10$^5$ CFU VPM1002 who showed the maximum size on Days 11 to 29. The size of the local induration is a measure of a local cellular immune response. The characteristic time profile in the VPM1002-groups differs from the time profile in the BCG-groups which is in accord with the pharmacodynamic immunogenicity results.

The correlation of Mean Induration Size by Treatment Group and Study Day is shown in FIG. 1.

The correlation of Mean Erythema Size by Treatment Group and Study Day is shown in FIG. 2.

Global tolerability was almost always assessed as good (42%) or very good (57%) by the subjects. Only 1 subject (BCG, no prior vaccination) rated the global tolerability as bad on Day 57, but no longer at 6 months after vaccination.

Laboratory data showed no clinically relevant time- or dose-related differences. Some subjects had values above the normal range already at baseline. Liver function parameter, especially ALT, increased above the normal range in some subjects (19 subjects, 13 BCG naïve subjects and 6 subjects with prior BCG vaccination). The number of subjects with abnormal ALT values after vaccination was highest in the group of subjects, who were BCG naïve and received 5×10$^5$ CFU VPM1002, but more pronounced increases were observed at the lower dose groups and never exceeded the 6-fold normal range and decreased until end of study.

Vital signs and ECG parameters showed no time- or dose-related differences.

No clinically relevant findings were observed in post-vaccination physical examination, liver sonography and chest X-ray. All QuantiFeron gold tests were negative.

15. Conclusions

Pharmacodynamics (Secondary Study Objective)

The secondary study objective was met.

VPM1002 shows immunogenicity as detected by dose-dependent IFN-γ stimulation. The results are shown in FIGS. 3 and 4.

VPM1002 induces quantitatively and qualitatively a different immune response than BCG.

VPM1002 has a boosting effect on an already existing, BCG induced, immune status.

Multifunctional CD4+ T cells were upregulated in all cohorts of VPM1002 (5×10$^5$ CFU). The results are shown in FIG. 5.

Safety (Primary Study Objective)

The primary study objective was met: Single vaccination with VPM1002 up to 5×10$^5$ CFU was safe and well tolerated.

Adverse events considered as drug-related were almost always injection site disorders. The number of AEs increased with dose and was similar after 5×10$^5$ CFU VPM1002 and the reference vaccine of 5×10$^{1'}$ CFU BCG.

The number and intensity of local reactions increased with dose of VPM1002, at the highest dose the incidence of local reactions was similar to that observed after vaccination with BCG.

Global tolerability of VPM1002 was always assessed as good or very good by the subjects.

Laboratory data, vital signs and ECG data showed no clinically relevant time- or dose-related differences.

16. Overall

The safety profile of VPM1002 was fine. VPM1002 showed immunogenicity. The immunogenic profile of VPM1002 differs from that of BCG. The benefit-risk-ratio allows for continuing the clinical development of this vaccine candidate.

LIST OF REFERENCES

1. World Health Organization (WHO) (2009). WHO Report 2009—Global tuberculosis control-epidemiology, strategy, financing. WHO, Geneva.
2. Andersen P. (2007). Tuberculosis vaccines—an update. Nat. Rev. Microbiol. 5, 484-487.
3. Mittrucker H W, Steinhoff U, Kohler A, Krause M, Lazar D, Mex P, Miekley D, Kaufmann S H. (2007). Poor correlation between BCG vaccination—induced T cell responses and protection against tuberculosis. Proc. Natl. Acad. Sci. U.S.A. 104, 12434-12439.
4. Young D, Dye C. (2006). The development and impact of tuberculosis vaccines. Cell. 124, 683-687.
5. Kaufmann S H. (2007). The contribution of immunology to the rational design of novel antibacterial vaccines. Nat. Rev. Microbiol. 5, 491-504.
6. Gagneux S, DeRiemer K, Van T, Kato-Maeda M, de Jong B C, Narayanan S, Nicol M, Niemann S, Kremer K, Gutierrez M C, Hilty M, Hopewell P C, Small P M. (2005). Variable host-pathogen compatibility in *Mycobacterium tuberculosis*. Proc. Natl. Acad. Sci. U.S.A. 103, 2869-2873.
7. Grode L, Seiler P, Baumann S, Hess J, Brinkmann V, Nasser Eddine A, Mann P, Goosmann C, Bandermann S, Smith D, Bancroft G J, Reyrat J M, van Soolongen D, Raupach B, Kaufmann S H. (2005). Increased vaccine efficacy against tuberculosis of recombinant *Mycobacterium bovis* bacille Calmette-Guérin mutants that secrete listeriolysin. The Journal of Clinical Investigation 115, 2472-2479.
8. Cho S, Mehra V, Thoma-Uszynski S, Stenger S, Serbina N, Mazzaccaro R J, Flynn J L, Barnes P F, Southwood S, Celis E, Bloom B R, Modlin R L, Sette A. (2000). Antimicrobial activity of MHC class I-restricted CD8+ T cells in human tuberculosis. Proc. Natl. Acad. Sci. U.S.A. 97, 12210-12215.
9. Winau F, Weber S, Sad S, deDiego J, Locatelli Hoops S, Breiden B, Sandhoff K, Brinkmann V, Kaufmann S H E, Schaible U E. (2006). Apoptotic vesicles crossprime CD8 T cells and protect against tuberculosis. Immunity. 24, 105-117.
10. Schaible U E, Winau F, Sieling P A, Fischer K, Collins H L, Hagens K, Modlin R L, Brinkmann V, Kaufmann S H. (2003). Apoptosis facilitates antigen presentation to T lymphocytes through MHC-I and CD1 in tuberculosis. Nat. Med. 9, 1039-1046.
11. Hess J, Miko D, Catic A, Lehmensiek V, Russel D, Kaufmann S H. (1998). *Mycobacterium bovis* bacille Calmette-Guérin strains secreting listeriolysin of *Listeria monocytogenes*. Proc Natl Acad Sci 95, 5299-5304.
12. Reyrat J M, Berthet F X, Gicquel B., (1995) The urease locus of *Mycobacterium tuberculosis* and its utilization for the demonstration of allelic exchange in *Mycobacterium bovis bacillus* Calmette-Guerin. Proc Natl Acad Sci USA. 92(19):8768-72
13. Brosch R, Gordon S V, Garnier T, Eiglmeier K, Frigui W, Valenti P, Dos Santos S, Duthoy S, Lacroix C, Garcia-Pelayo C, Inwald J K, Golby P, Garcia J N, Hewinson R G, Behr M A, Quail M A, Churcher C, Barrell B G, Parkhill J, Cole S T, Proc Natl Acad Sci USA. 2007 Mar. 27; 104(13): 5596-601. Epub 2007 Mar. 19.

The invention claimed is:

1. Vaccine for use in humans comprising as an active ingredient a recombinant *Mycobacterium* which is urease-deficient and which comprises a recombinant nucleic acid molecule encoding a fusion polypeptide comprising (a) a *Mycobacterium* antigen Ag85B or an immunogenic fragment thereof comprising a peptide sequence encoded by nucleotides 121-153 of SEQ ID NO:1, and (b) a phagolysomal escape domain comprising a peptide encoded by nucleotides 211-1722 of SEQ ID NO:1, wherein the recombinant *Mycobacterium* is a recombinant *Mycobacterium bovis* (BCG) cell from strain Danish subtype Prague and wherein the recombinant *Mycobacterium* cell does not carry an antibiotic resistance gene.

2. The vaccine of claim 1, which is for administration to a *Mycobacterium*-naïve subject.

3. The vaccine of claim 1, which is for administration to a *Mycobacterium*-pre-exposed subject.

4. The vaccine of claim 1, which is a lyophylisate optionally together with a reconstruction fluid.

5. The vaccine of claim 1, which comprises a dose of about $10^3$-$10^4$ CFU, about $10^4$-$10^5$ CFU or about $10^5$-$10^6$ CFU.

6. The vaccine of claim 1 for intradermal administration.

7. The vaccine of claim 1 for administration in a single dose or for administration as two or more doses.

8. The vaccine of claim 1 for the upregulation of multifunctional $CD4^+$ T cells.

9. The vaccine of claim 1 for use against tuberculosis.

10. A method for vaccinating a human subject, comprising administering a pharmaceutically effective dose of a recombinant *Mycobacterium* which is urease-deficient and which comprises a recombinant nucleic acid molecule encoding a fusion polypeptide comprising (a) a *Mycobacterium* antigen Ag85B or an immunogenic fragment thereof comprising a peptide sequence encoded by nucleotides 121-153 of SEQ ID NO:1, and (b) a phagolysomal escape domain comprising a peptide encoded by nucleotides 211-1722 of SEQ ID NO:1, wherein the recombinant *Mycobacterium* is a recombinant *Mycobacterium bovis* (BCG) cell from strain Danish subtype Prague and wherein the recombinant *Mycobacterium* cell does not carry an antibiotic resistance gene.

11. The vaccine of claim 2, wherein said *Mycobacterium*-naïve subject is a newborn.

* * * * *